US00PP27023P3

(12) United States Plant Patent
Olesen

(10) Patent No.: US PP27,023 P3
(45) Date of Patent: Aug. 9, 2016

(54) CLIMBING ROSE PLANT NAMED 'POULCY031'

(50) Latin Name: ***Rosa* hybrid**
Varietal Denomination: Poulcy031

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 14/121,288

(22) Filed: Aug. 15, 2014

(65) Prior Publication Data

US 2016/0050803 P1 Feb. 18, 2016

(51) Int. Cl.
*A01H 5/02* (2006.01)

(52) U.S. Cl.
USPC ..... Plt./114

(58) Field of Classification Search
USPC ..... Plt./114, 109
CPC ..... A01H 5/0222; A01H 5/0216
See application file for complete search history.

(56) References Cited

PUBLICATIONS http://www.poulsenroser.dk/media/73071/COURTYARD-Climbers-2013_LR_Poulsen-Roser.pdf; 2012; 1 page.*

* cited by examiner

*Primary Examiner* — Kent L Bell

(57) ABSTRACT

A new garden rose plant of the Climbing class which has abundant, pink blend flowers and attractive foliage. This new and distinct variety has shown to be uniform and stable in the resulting generations from asexual propagation.

3 Drawing Sheets

Botanical designation: *Rosa* hybrid.
Variety denomination: 'Poulcy031'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2005 and the resulting seeds were planted in a controlled environment in Fredensborg, Denmark. The new variety, named 'Poulcy031', originated as a single seedling from the stated cross.

The new variety may be distinguished from its male pollen parent and female seed parent primarily by the following characteristics. The female seed parent has white flowers, while the new variety has pink blend flowers. The male pollen parent has medium red flowers.

The objective of the hybridization of this rose variety was to create a new and distinct variety for garden use with unique qualities, such as:

1. Uniform and abundant pink blend flowers;
2. Vigorous, but compact growth when propagated both as a budded rose and on its own roots;
3. Exceptional disease resistance; and
4. Reduced apical dominance in flowering habit. The new variety produces flowers more evenly from the lower branches to the top of the plant than other climbing rose varieties.

This combination of qualities is not present in previously available commercial cultivars of this type, known to the inventor, and distinguish 'Poulcy031' from all other varieties of which we are aware.

As part of the rose development program, Mogens N. Olesen germinated the seeds from the aforementioned hybridization during winter of 2005 and conducted evaluations on the resulting seedlings in a controlled environment in Fredensborg, Denmark. 'Poulcy031' was selected in the spring of 2006 by the inventor as a single plant from the progeny of the aforementioned hybridization.

Asexual reproduction of 'Poulcy031' by traditional budding and rooted cuttings was first done by Mogens N. Olesen in the nursery in Fredensborg, Denmark in July, 2006. This initial and other subsequent asexual propagations conducted in controlled environments have demonstrated that the characteristics of 'Poulcy031' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy031'.

Specifically illustrated in FIG. 1 are petals detached, and flower buds.

DETAILED DESCRIPTION OF THE VARIETY

Figure 1:
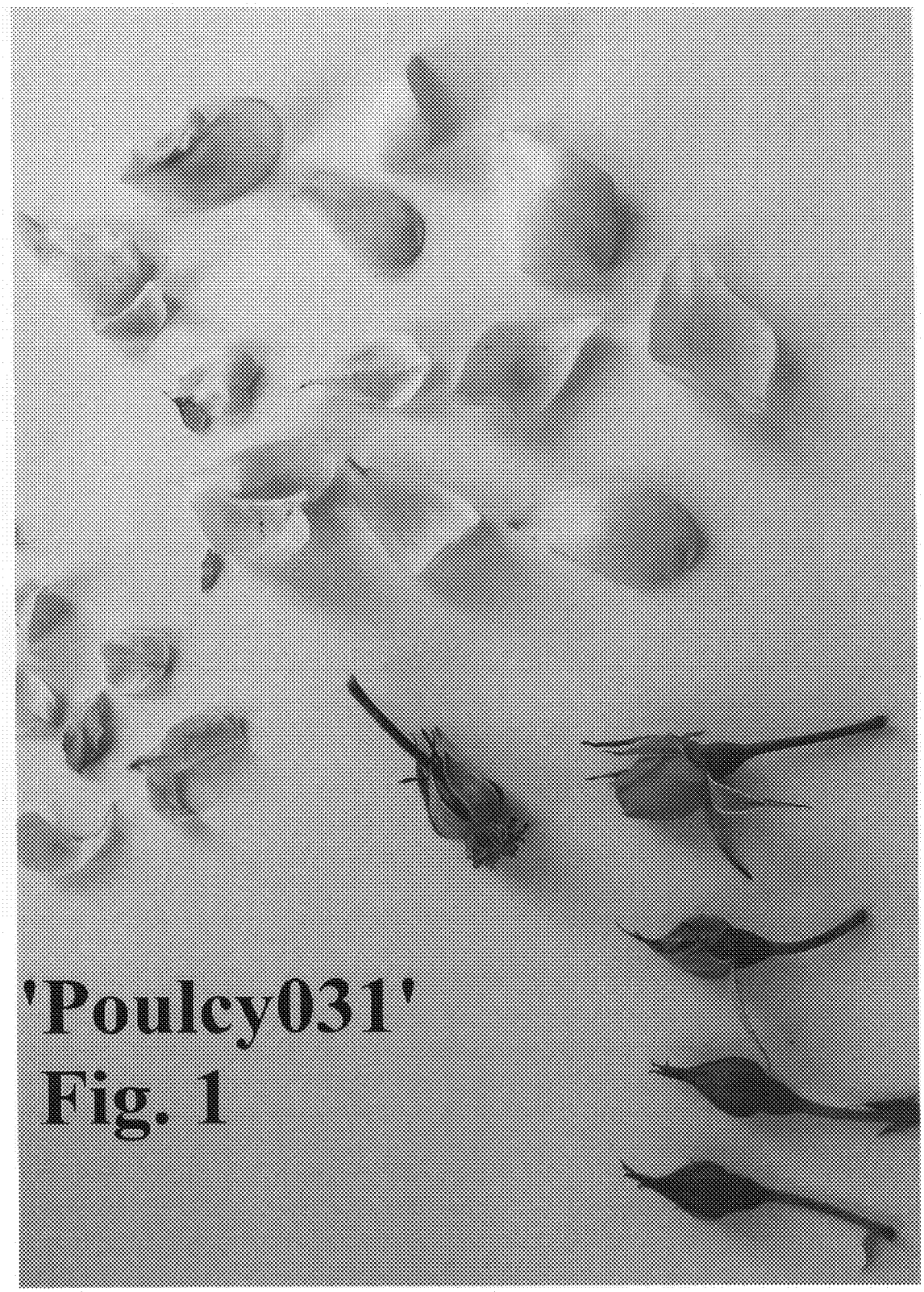
Figure 2:
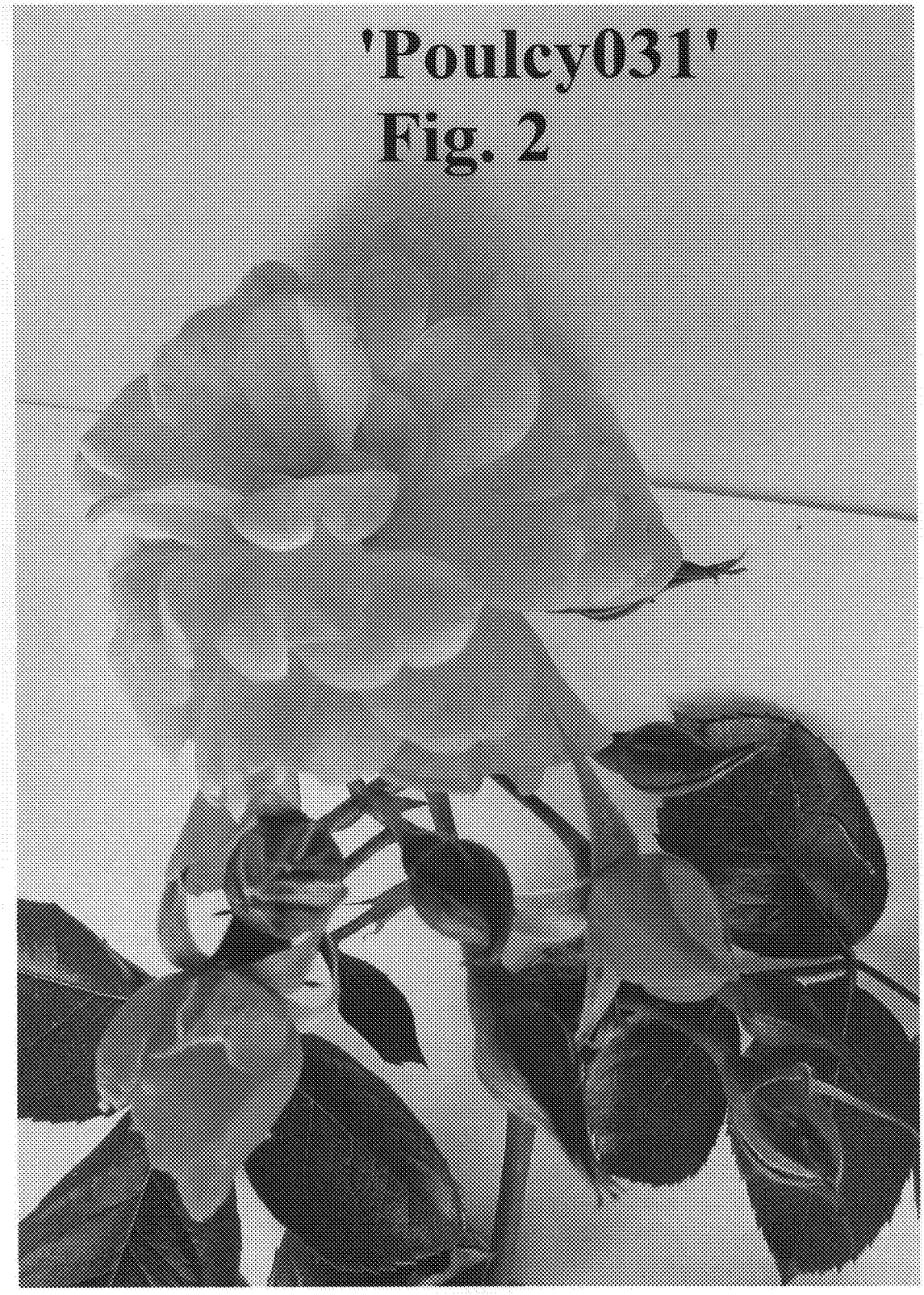
FIG. 2 shows open flower and flowers upon opening.
Figure 3:
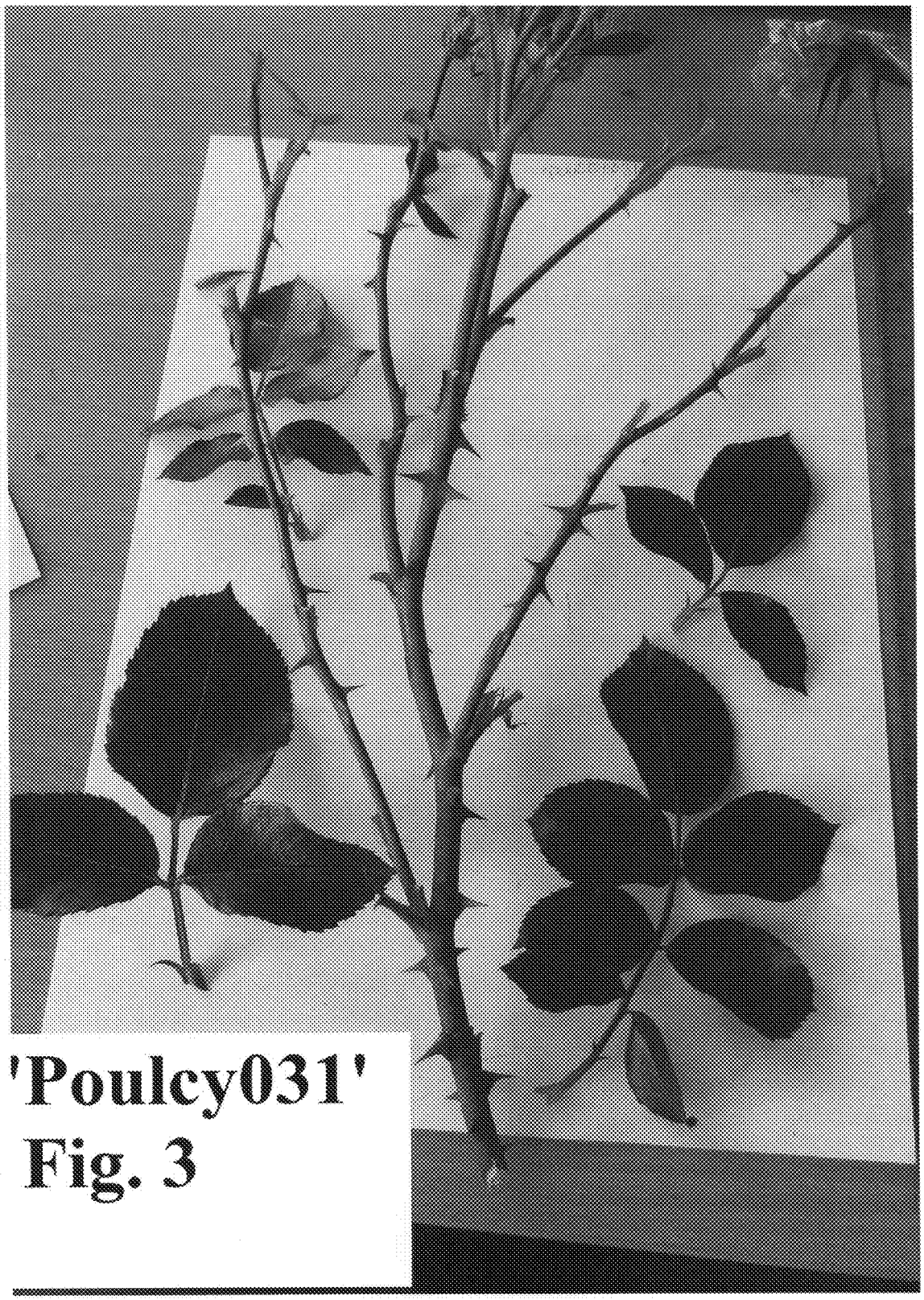
FIG. 3 shows the stems leaves, and peduncles. Plants shown are 2 years of age.

The following is a description of 'Poulcy031', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulyc003', U.S. Plant Pat. No. 15,106 dated Aug. 24, 2006 are compared to 'Poulcy031' in Chart 1.

CHART 1

| | 'Poulcy031' | 'Poulyc003' |
|---|---|---|
| Petal Count | 30 to 40 petals | 70-80 petals |
| Flower Diameter | 60 to 90 mm | 40 mm |
| General Tonality of Flower Color | Red Group 49A to Red Group 49B | Yellow-Orange Group 14D |

FLOWER AND FLOWER BUD

Blooming habit: Continuous.

Flower bud:

*Size.*—Upon opening, 27 mm in length from base of receptacle to end of bud. Bud diameter is 10 mm.

*Bud form.*—Ovoid.

*Bud color.*—As sepals divide petals are Red Group 42C.

*Sepal inner surface.*—Color: Yellow-Green Group 146C. Surface: Lightly pubescent.

*Sepal outer surface.*—Color: Yellow-Green Group 146B. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—23 mm long, 7 mm wide.

*Receptacle.*—Texture: Smooth. Size: 7 mm in height, 7 mm wide. Color: Yellow-Green Group 146C. Shape: Campanulate.

*Pedicel.*—Surface: Smooth. Length: 20 to 30 mm. Diameter: 3 mm on average. Color: Yellow-Green Group 146C. Strength: Moderate.

*Peduncle.*—Length: 2 to 23 cm. Diameter: About 2 to 3 mm. Color: Yellow-Green Group 146A. Texture: Smooth.

Flower bud development: Flower buds are borne in clusters of 5 to 9 flower buds per stem. Development as a panicle.

Flower bloom:

*Fragrance.*—Light floral.

*Duration.*—The blooms have a duration on the plant of approximately 7 to 10 days. Petals do not drop easily after flowers have fully matured.

*Size.*—Flower diameter is 60 to 90 mm when open. Flower depth is 30 mm.

*Flower shape.*—Semi double flower, with petals that curve out from the center.

*Shape of flower, side view.*—The upper portion is flat. The lower portion is concave.

Petalage: Under normal conditions, flowers have 30 to 40 petals.

General tonality of flower: Open flowers are Red Group 49A to Red Group 49B.

Petal color:

*Upon opening, outer petals.*—Upper surface: Orange-Red Group 33B. At the basal zone Yellow-Orange Group 23B. Lower surface: Orange-Red Group 33C. At the basal zone Yellow-Orange Group 23B.

*After opening, outer and inner petals.*—Upper surface: Red Group 49A. Lower surface: Red Group 49D.

*Basal petal spots, after opening.*—Upper surface: Yellow-Orange Group 19B. Lower surface: Yellow-Orange Group 19B.

Petals:

*Petal reflex.*—Weak.

*Margin.*—Entire and uniform. Weak undulations.

*Shape.*—Generally narrow and broad elliptic. Apex shape: Rounded. Base shape: Acute.

*Size.*—35 mm (l)×mm 27 (w).

*Texture.*—Smooth, occasionally somewhat rough in texture.

*Thickness.*—Thin.

Petaloids:

*Size.*—17 mm (l) by 10 mm (w).

*Quantity.*—About 4.

*Shape.*—Irregular, asymmetric. Apex is acute. Base is acute.

*Color.*—Upper surface is Red Group 49A. Lower surface is Red Group 49D. Basal petal spots are Yellow-Orange Group 19B.

Reproductive flower parts:

*Pollen.*—None observed.

*Anthers.*—Size: 1 mm in length. Color: Orange-Red Group 34B. Quantity: 100 on average.

*Filaments.*—Color: Yellow-Orange Group 22A. Length: 5 mm.

*Pistils.*—Length: 5 mm. Quantity: 30 on average.

*Stigmas.*—Color: Orange Group 24B.

*Styles.*—Color: Yellow-Orange Group 22B.

*Location of stigmas.*—Level in location relative to the length of the filaments and the height of the anthers.

*Hips.*—None Observed.

PLANT

Plant growth: Bushy and arching. Plants are 200 cm in height, and 100 cm wide.

Stems:

*Color.*—Juvenile growth: Yellow-Green Group 146A. Mature growth: Yellow-Green Group 146C.

*Length.*—On average, canes are 50 cm from the base of the plant to the flowering portion.

*Diameter.*—7 mm.

*Internodes.*—On mature canes about 30 mm between nodes.

Surface texture.—Young wood: Smooth. Older wood: Smooth.

Long prickles:

*Incidence.*—10 prickles per 10 cm of stem.

*Size.*—Average length of prickles on mature stems is 10 mm.

*Shape.*—Upper portion is concave. Lower portion is concave.

*Color.*—Juvenile prickles: Greyed-Orange Group 176C. Mature prickles: Greyed-Orange Group 177A.

Plant foliage:

*Compound leaf.*—120 mm (l)×110 (w).

*Quantity.*—2 to 4 leaves per 10 cm of stem on average.

*Leaf bearing angle to the stem.*—90 degrees.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 147B.

Plant leaves and leaflets:

*Stipules*.—Size: 20 mm long, 5 mm wide. Quantity: 2 per compound leaf. Shape: Linear, slightly broad based with outward extending apices. Margins: Finely serrated. Color: Yellow-Green Group 144A with some intonations of Greyed-Red Group 178A.

*Petiole*.—Length: 20 mm. Diameter: 2 mm.

*Upper surface*.—Color: Yellow-Green Group 146B with intonations of Greyed-Red Group 178A.

*Lower surface*.—Color: Yellow-Green Group 146B.

*Rachis*.—Length: 20 mm. Upper surface: Color: Yellow-Green Group 147A with some intonations of Greyed-Red Group 178A.

*Lower surface*.—Color: Yellow-Green Group 146B. Observations: Small prickles.

*Leaflet*.—Quantity: Normally 5 to 7 leaflets. Margins: Serrulate. Size: On average terminal leaflets are 50 mm long, 40 mm wide. Shape: Generally ovate. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon Rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Climbing rose class named 'Poulcy031', substantially as illustrated and described herein, due to its abundant pink blend flowers, disease resistance, and extended period of bloom.

* * * * *

'Poulcy031'

'Poulcy031'

'Poulcy031'